(12) United States Patent
Potnis et al.

(10) Patent No.: US 11,666,107 B2
(45) Date of Patent: Jun. 6, 2023

(54) APPARATUS, SYSTEMS, AND METHODS FOR SEALING AN INTERFACE

(71) Applicant: O&M Halyard, Inc., Mechanicsville, VA (US)

(72) Inventors: Prasad S. Potnis, Johns Creek, GA (US); Christena K. Nash, Alpharetta, GA (US); Dennis Joseph, Milton, GA (US); Brian E. Lin, Cumming, GA (US); Namita A. Mithani, Alpharetta, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 12 days.

(21) Appl. No.: 16/851,396

(22) Filed: Apr. 17, 2020

(65) Prior Publication Data

US 2020/0359720 A1    Nov. 19, 2020

Related U.S. Application Data

(60) Provisional application No. 62/870,098, filed on Jul. 3, 2019, provisional application No. 62/848,639, filed on May 16, 2019.

(51) Int. Cl.
*A41D 19/00* (2006.01)
*A41D 13/08* (2006.01)
(Continued)

(52) U.S. Cl.
CPC ..... *A41D 19/0089* (2013.01); *A41D 19/0048* (2013.01); *A41D 13/08* (2013.01); (Continued)

(58) Field of Classification Search
CPC ............ A41D 19/0048; A41D 19/0089; A41D 19/015; A41D 13/1227; A61F 15/004
(Continued)

(56) References Cited

U.S. PATENT DOCUMENTS 3,457,919 A * 7/1969 Harbard ................ A61F 13/023
602/55
3,747,126 A 7/1973 Hoagland
(Continued)

FOREIGN PATENT DOCUMENTS

DE    9214949 U1    3/1994
EP    0752892 B1 *  7/2001  ....... A61F 13/15658
GB    1132599 A    11/1968

OTHER PUBLICATIONS

International Search Report and Written Opinion for PCT/US2020/028637, dated Jul. 13, 2020, 14 pages.

*Primary Examiner* — Jameson D Collier
*Assistant Examiner* — Matthew R Marchewka
(74) *Attorney, Agent, or Firm* — Dority & Manning, P.A.

(57) ABSTRACT

A protective guard is provided for sealing an interface. The protective guard includes a body having a fluid impervious material and proximal and distal segments that may comprise a superabsorbent or a non-superabsorbent material. The proximal and distal segments are positioned on first and second sides, respectively, of the interface. The protective guard extends about the interface to create a fluid barrier. In some embodiments, the non-superabsorbent material may be an elastic material, such as an elastic band, and in particular embodiments, the non-superabsorbent material may be nitrile. In further embodiments, the non-superabsorbent material may be an expandable material that expands upon contact or interaction with a fluid.

19 Claims, 7 Drawing Sheets

(51) Int. Cl.
*A61B 42/00* (2016.01)
*A41D 19/015* (2006.01)
*B29L 31/48* (2006.01)

(52) U.S. Cl.
CPC ............ *A41D 19/015* (2013.01); *A61B 42/00* (2016.02); *B29L 2031/4864* (2013.01)

(58) Field of Classification Search
USPC .............................. 2/16, 161.3, 161.7, 161.8
See application file for complete search history.

(56) References Cited

U.S. PATENT DOCUMENTS

| | | | | |
|---|---|---|---|---|
| 3,852,823 | A * | 12/1974 | Jones ....................... | A42B 1/12 428/41.9 |
| 4,133,624 | A * | 1/1979 | Heavner ................. | B29C 41/14 425/275 |
| 4,464,796 | A * | 8/1984 | Heissenberger ... | A41D 19/0062 2/162 |
| 5,150,475 | A * | 9/1992 | Hansen ................ | A41D 13/088 2/16 |
| 5,555,561 | A | 9/1996 | Plachta et al. | |
| 5,592,953 | A * | 1/1997 | Delao ................... | A61F 15/004 128/882 |
| 5,628,067 | A | 5/1997 | Meyer et al. | |
| 5,734,992 | A | 4/1998 | Ross | |
| 5,924,130 | A | 7/1999 | Fragomeli | |
| 5,948,707 | A * | 9/1999 | Crawley ................ | B32B 27/12 442/101 |
| 6,092,237 | A | 7/2000 | Baldwin | |
| 6,122,772 | A | 9/2000 | De Guzman | |
| 6,941,579 | B2 | 9/2005 | Tanenbaum | |
| 7,269,859 | B2 | 9/2007 | Wells | |
| 7,451,497 | B2 | 11/2008 | Von Blücher | |
| 8,529,481 | B1 | 9/2013 | Lois | |
| 9,101,509 | B2 | 8/2015 | Rogers | |
| 2002/0082542 | A1 * | 6/2002 | Hall ....................... | B32B 27/12 602/60 |
| 2003/0233695 | A1 | 12/2003 | Golde | |
| 2005/0118383 | A1 * | 6/2005 | Cargill ..................... | A61F 7/02 428/68 |
| 2005/0267428 | A1 * | 12/2005 | Ashton ............. | A61F 13/49466 604/385.12 |
| 2005/0268941 | A1 * | 12/2005 | McKenzie ............. | A47L 13/18 134/6 |
| 2006/0084904 | A1 * | 4/2006 | Ritchey ................. | A61F 15/004 602/60 |
| 2006/0085884 | A1 * | 4/2006 | Giacheri ............... | A41D 31/18 2/24 |
| 2006/0085887 | A1 | 4/2006 | Palomo et al. | |
| 2007/0088281 | A1 | 4/2007 | Ritchey | |
| 2010/0017939 | A1 | 1/2010 | Carpenter, Jr. | |
| 2011/0239349 | A1 | 10/2011 | Thompson | |
| 2012/0030853 | A1 * | 2/2012 | Mountfort ............. | A41D 19/01 2/158 |
| 2013/0019374 | A1 * | 1/2013 | Schwartz ............. | A61F 13/041 428/492 |
| 2014/0157475 | A1 | 6/2014 | Smith et al. | |
| 2015/0119774 | A1 | 4/2015 | Rogers | |
| 2016/0376476 | A1 * | 12/2016 | Taha .................. | A41D 13/1209 156/249 |
| 2019/0053551 | A1 * | 2/2019 | Jascomb ................ | B32B 27/20 |

\* cited by examiner

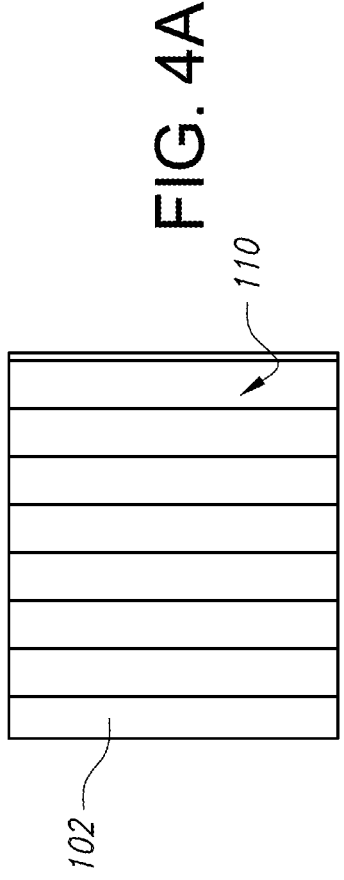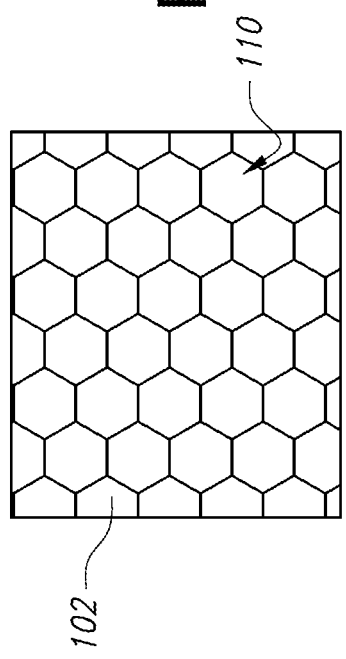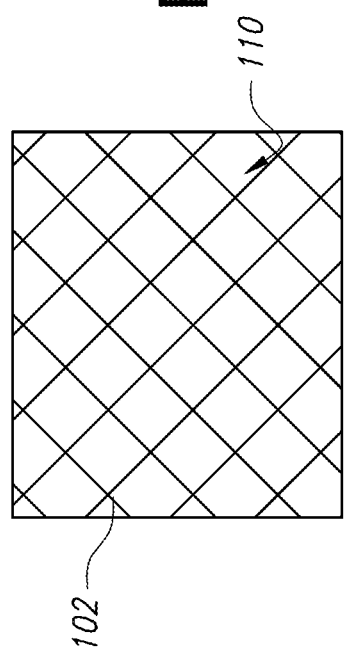

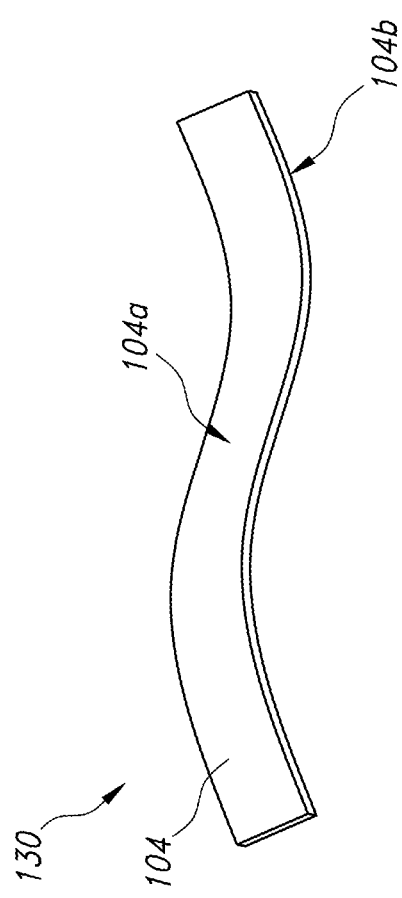
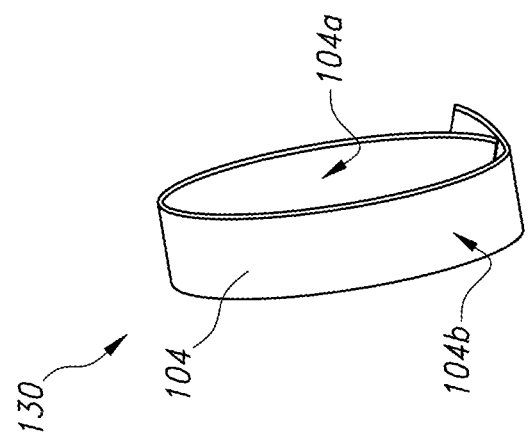
FIG. 7A
FIG. 7B

APPARATUS, SYSTEMS, AND METHODS FOR SEALING AN INTERFACE

RELATED APPLICATIONS

The present application claims priority to U.S. Provisional Application Ser. No. 62/848,369, filed on May 16, 2019, and U.S. Provisional Application Ser. No. 62/870,098, filed on Jul. 3, 2019, which are incorporated herein in their entirety by reference thereto.

FIELD

The subject matter of the present disclosure relates generally to protective guards and, more particularly, to apparatus, systems, and methods for sealing an interface, such as an interface between a surgical gown and a glove.

BACKGROUND

Some medical procedures expose healthcare providers to a higher risk of exposure to bodily fluids, such as a patient's blood. Personal protective equipment (PPE), such as gloves, gowns, and/or long-sleeved surgical suits, is designed to limit or prevent such exposure. For example, gloves are designed to fit over surgical gown sleeves, but typically, gloves do not provide a sealed interface between the gown and glove. In fact, many times, bunching of the gown sleeve under the glove can create a channeling effect where fluids can follow the bunching of the sleeve and flow underneath the glove, exposing a healthcare provider's bare hands and/or arms to the patient's bodily fluids, which could lead to contamination and/or infection of the healthcare provider. In addition, the glove cuff can sometimes slide down on itself, decreasing its protective area. Although improvements have been made to the materials and designs of both surgical gowns and surgical gloves, little attention has been paid to the junction or interface between the sleeve of the gown and the glove, known as the gown-glove interface. Often, it is at the gown-glove interface that body fluids or bloodborne pathogens, which may contain harmful or infectious diseases, may breach the protective equipment worn by the healthcare provider.

Consequently, there is a need for an improved barrier against bodily fluids and/or other contaminants. In particular, a protective guard that covers around an interface between two interfacing items, such as a surgical gown and glove, to seal the interface would be desirable. More particularly, a protective guard incorporating a fluid impervious body that stretches to provide a customizable and/or compressive fit would be useful. Additionally or alternatively, a protective guard having a superabsorbent material for absorbing and containing fluid such that the fluid may not flow to the interface would be advantageous. Additionally or alternatively, a cuff comprising the fluid impervious body of the protective guard and/or a tape comprising the superabsorbent material of the protective guard also would be beneficial.

SUMMARY

Additional aspects and advantages of the invention will be set forth in part in the following description, may be apparent from the description, or may be learned through practice of the invention.

In one aspect, the present subject matter is directed to a protective guard for sealing an interface. The protective guard comprises a body comprising a fluid impervious material, a proximal segment, and a distal segment. The proximal segment is positioned on a first side of the interface, and the distal segment is positioned on a second side of the interface. The protective guard extends about the interface to create a fluid barrier.

It should also be understood that the protective guard may further include any of the additional features as described herein. For example, in some embodiments, the fluid impervious material is hydrophobic. In further embodiments, the fluid impervious material has elasticity. In exemplary embodiments, the fluid impervious material is nitrile.

In yet further embodiments, at least one of the proximal segment and the distal segment comprises an outer surface having a first raised pattern. In some embodiments, the first raised pattern comprises vertical striations. In other embodiments, the first raised pattern comprises a honeycomb pattern. In still other embodiments, the first raised pattern comprises cross-hatching.

In still further embodiments, at least one of the proximal segment and the distal segment comprises an inner surface having a second raised pattern. In some embodiments, the second raised pattern comprises pyramidal shaped nubs. In other embodiments, the second raised pattern comprises X shaped nubs.

In some embodiments, the proximal segment is positioned at a user's hand. In further embodiments, the proximal segment comprises an elastic material. In yet further embodiments, the distal segment comprises nitrile. In still further embodiments, at least one of the proximal segment and the distal segment comprises a non-superabsorbent material that expands upon contact with a fluid.

In another aspect, the present subject matter is directed to a protective guard for sealing an interface. The protective guard comprises a body comprising a fluid impervious material, a proximal segment comprising an elastic material, and a distal segment comprising nitrile. The proximal segment is positioned on a first side of the interface, and the distal segment is positioned on a second side of the interface. The protective guard extends about the interface to create a fluid barrier.

It should also be appreciated that the cuff may further include any of the additional features as described herein. For instance, in some embodiments, the fluid impervious material is a fluid impervious film. In further embodiments, at least one of an inner surface and an outer surface of the proximal segment has a raised pattern. In still further embodiments, at least one of an inner surface and an outer surface of the distal segment has a raised pattern.

In still another aspect, the present subject matter is directed to a protective guard for sealing an interface. The protective guard comprises a body comprising a fluid impervious material, a proximal segment comprising a non-superabsorbent expandable material, and a distal segment comprising the non-superabsorbent expandable material. The non-superabsorbent expandable material expands upon contact with a fluid. The proximal segment is positioned on a first side of the interface and the distal segment is positioned on a second side of the interface. Further, the protective guard extends about the interface to create a fluid barrier. It should also be understood that the tape may further include any of the additional features as described herein.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIGS. 4A, 4B, and 4C provide schematic views of a first raised pattern for an outer surface of the protective guard of FIG. 1, according to various exemplary embodiments of the present subject matter.

FIGS. 7A and 7B each provide a schematic view of a tape for sealing an interface, according to an exemplary embodiment of the present subject matter.

DETAILED DESCRIPTION

Figure 1:
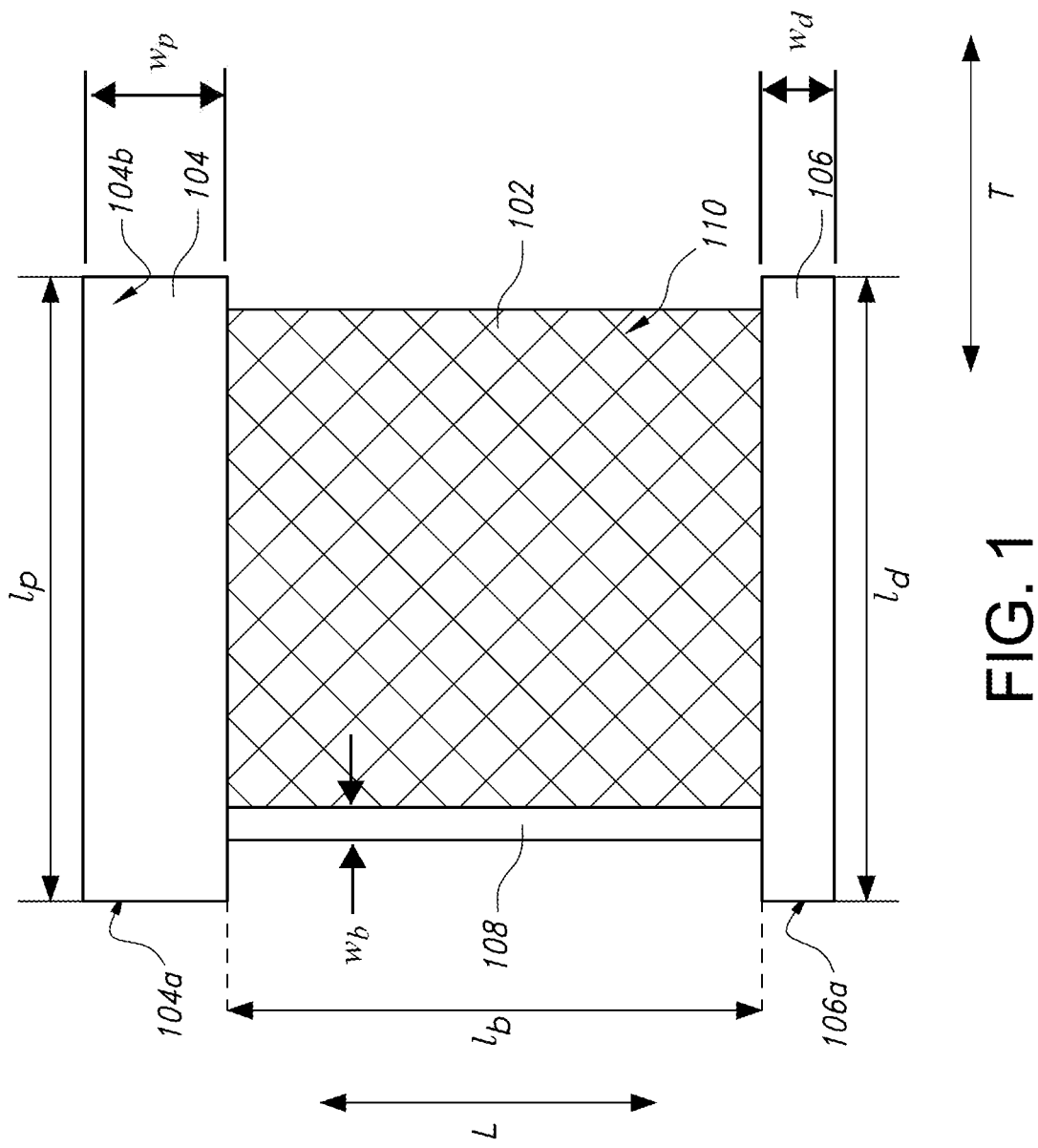
FIG. 1 provides a schematic view of a protective guard for sealing an interface, according to an exemplary embodiment of the present subject matter.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value may be raised or lowered by 5% and remain within the disclosed embodiment. Further, for the purposes of this description, proximal generally indicates that portion of a component next to or nearer to a hand of a wearer (when the component is in use), while the term distal generally indicates a portion further away from the hand of a wearer and nearer to the body of the wearer (when the component is in use).

Described herein are protective guards, cuffs, tapes, or similar accessories suitable for use in a variety of procedures for sealing an interface and preventing the ingress of fluid. While described in conjunction with its use in surgical room procedures located in hospitals, ambulatory surgical facilities, or the like, the present subject matter is intended for use wherever there is a need for preventing fluid from entering an interface. Consequently, the following description should not be considered a limitation as to the scope of use of the present subject matter.

Generally, the present subject matter provides apparatus and methods for providing a fluid impervious seal. For example, the present subject matter provides a protective guard for sealing an interface. The protective guard may be configured as a protective gauntlet that surrounds an interface between a surgical gown and a glove to seal the interface between the gown and glove. The protective guard may comprise a body comprising a fluid impervious material, a proximal segment comprising a superabsorbent material, and a distal segment comprising the superabsorbent material. The proximal segment may be positioned on a first side of the interface, e.g., at or near a bottom portion of a user's hand, and the distal segment is positioned on a second side of the interface, e.g., at the user's forearm or above the user's elbow. The protective guard may extend about the interface to create a fluid barrier. For instance, the fluid impervious body may prevent fluids, such as a patient's bodily fluids, from penetrating the body of the protective guard and also may channel or guide the fluids toward the proximal segment and/or the distal segment, where are positioned at each end of the body. The superabsorbent material of the proximal and/or distal segments may absorb and contain the fluids. Further, the proximal and/or distal segments may comprise an adhesive that adheres the segment(s) to an underlying or overlying material, such as the gown or the glove, and thereby creates a seal between the segment(s) and the underlying or overlying material that helps prevent fluid from seeping between the segment(s) and the underlying or overlying material. The protective guard also may comprise a body segment of the superabsorbent material that is positioned on the body of the protective guard to help absorb and contain fluid. Moreover, the protective guard also may comprise layers of superabsorbent material having different fluid absorption rates in order to control the flow and absorption of fluid by the protective guard. These and other features as described herein can help prevent fluid from reaching the interface between the interfacing items, e.g., the gown and the glove, and thereby help prevent fluid from flowing into the interface and potentially contaminating whatever is beyond the interface, e.g., a surgeon's bare skin.

Referring now to the figures, FIG. 1 provides a schematic view of a protective guard for sealing an interface. The protective guard 100 includes a body 102 comprising a fluid impervious material, a proximal segment 104 comprising a superabsorbent material, and a distal segment 106 comprising the superabsorbent material. The proximal segment 104 and the distal segment 106 each extend along a transverse direction T, and the body 102 extends from the proximal segment 104 to the distal segment 106 along a longitudinal direction L. In exemplary embodiments, such as illustrated in FIG. 1, a body segment 108 of the superabsorbent material extends lengthwise from the proximal segment 104 to the distal segment 106 along the longitudinal direction L. The body segment 108 has a length $l_b$ along the longitudinal direction L. In the depicted embodiment, it will be appreciated that the body segment length $l_b$ is the same as a length of the body 102 along the longitudinal direction L. Moreover, although illustrated as a strip of material, the body segment 108 may have any suitable shape and/or size.

The proximal segment 104 may be positioned on a first side 103 of the interface 101, and the distal segment 106 may be positioned on a second side 105 of the interface 101. Further, the protective guard 100 may extend about the interface 101 to create a fluid barrier. More particularly, the protective guard 100 extends about the interface 101 such that the body 102 of the protective guard 100 covers the interface 101 to provide a seal at the interface, and the proximal and distal segments 104, 106 extend about the first and second sides 103, 105, respectively, to provide a seal on each side of the interface 101.

The fluid impervious material from which the body 102 is formed may be, e.g., hydrophobic fluid impervious material and, in some embodiments, may have elasticity. One example of a hydrophobic fluid impervious material with elasticity is nitrile. Other fluid impervious materials may be used as well. For example, the body 102 may be formed from a liquid impervious material such as, but not limited to, polyurethane film; silicone, nitrile, latex, or other elastomeric materials; nonwoven barrier fabrics; or a combination thereof. The nonwoven barrier fabrics may include spunbond-meltblown-spunbond ("SMS") laminate fabrics, which may optionally be coupled with one or more elastic film layers in order to enhance the elasticity and flexibility of the nonwoven barrier fabric. Such nonwoven barrier fabrics may be moisture-vapor breathable while still maintaining a liquid impervious barrier. For a general description of nonwoven barrier fabrics see U.S. Patent Application Publication 2019/0053551, which is herein incorporated by reference.

Moreover, the superabsorbent material from which the proximal segment 104, the distal segment 106, and the body segment 108 are formed may be, e.g., a superabsorbent adhesive. The adhesive of the superabsorbent material may be activated by different chemistries, e.g., air, water, etc. For instance, the superabsorbent material may be configured to swell when exposed to one or more fluids, such as blood and/or other bodily fluids, thereby creating a better pressure seal by tightening the protective guard 100 around the interface 101. As an example, an exemplary superabsorbent adhesive forming the proximal segment 104, the distal segment 106, and/or the body segment 108 may react with the water in blood to quickly polymerize and create a seal. Thus, the inclusion of the superabsorbent material in the protective guard 100 helps tighten the fit of the protective guard 100 after the superabsorbent material absorbs fluid, which may improve the sealing capability of the protective guard 100. Additionally or alternatively, different superabsorbent materials may be used in the various portions of the protective guard 100, e.g., the proximal segment 104, distal segment 106, and body segment 108, which have different fluid flow or absorption characteristics, in order to direct or control the flow and/or absorption of fluid by the protective guard 100. For instance, an outer layer such as the proximal segment 104 may be formed from a quicker absorbing superabsorbent material, and an inner layer such as the body segment 108 may be formed from a superabsorbent material configured to act as a reservoir for fluid, in order to provide continuous fluid flow control during a surgical procedure. In some embodiments, the superabsorbent material may be coated onto an elastic substrate, such that the proximal segment 104, the distal segment 106, and/or the body segment 108 may stretch and/or otherwise deform, e.g., to customize the fit of the protective guard 100, to secure the protective guard 100 in place about the interface 100, and/or to help ensure the protective guard 100 seals the sides 103, 105 of the interface. In particular exemplary embodiments, the superabsorbent material may be coated onto an underside of or the inner surface 104a of the proximal segment 104, the inner surface 106a of the distal segment 106, and/or the inner surface 110 of the body segment 108 of the protective guard 100.

In some embodiments, in addition to or in lieu of comprising an adhesive, the proximal segment 104 and/or the distal segment 106 may be formed from a material that sticks to itself, e.g., such that the proximal segment 104 and/or the distal segment 106 may be wrapped back on itself to form a pressure seal. In other embodiments, in addition to or in lieu of comprising an adhesive, the proximal segment 104 and/or the distal segment 106 may comprise hooks formed, e.g., in a substrate supporting the superabsorbent material, that catch on material such as the material from which the gown 116 is made to secure the proximal segment 104 and/or the distal segment 106 in place. In still other embodiments, in addition to or in lieu of comprising an adhesive, other types of fasteners, such as hook and loop fasteners, ties, snaps, etc. may be used to secure the proximal segment 104 and/or the distal segment 106 to itself and/or to another component, such as the gown 116 or glove 112.

Figure 2:
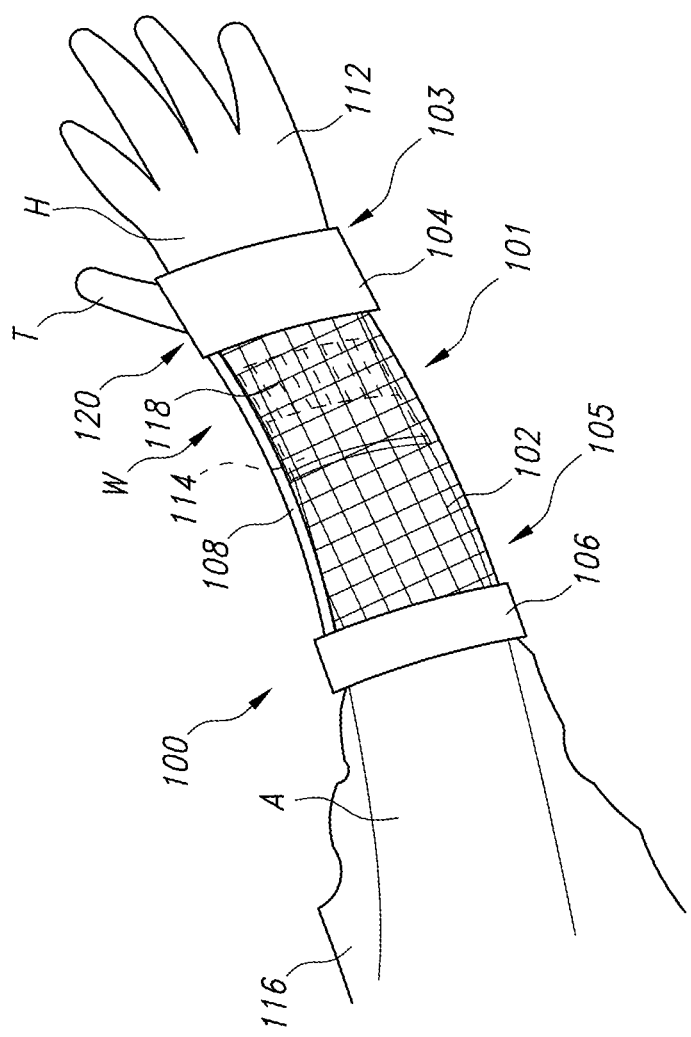
FIG. 2 provides a schematic view of the protective guard of FIG. 1 configured for sealing the interface between a surgical gown and a glove, where the protective guard overlies both the gown and the glove, according to an exemplary embodiment of the present subject matter.
Figure 3:
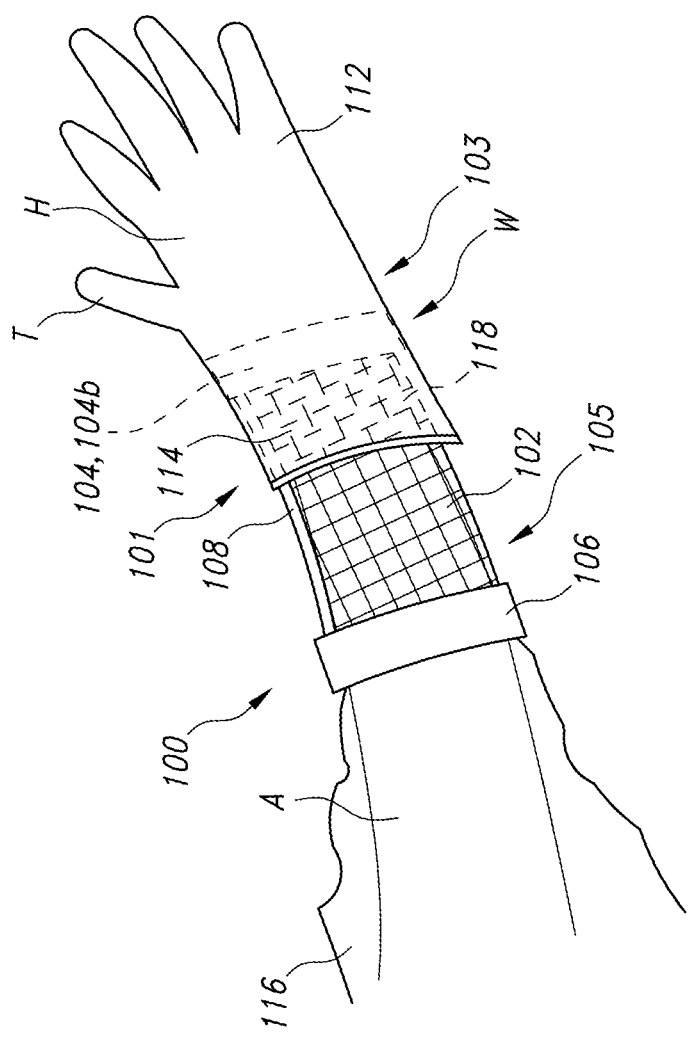
FIG. 3 provides a schematic view of the protective guard of FIG. 1 configured for sealing the interface between a surgical gown and a glove, where the protective guard overlies the gown and underlies the glove, according to an exemplary embodiment of the present subject matter.

Referring to FIGS. 2 and 3, in some embodiments, the seal may be formed between wearable items such as a glove 112 and a gown 116 worn by a surgeon in a surgical setting. In such embodiments, the interface 101 may be the interface between a cuff 114 of the glove 112 and a cuff 118 of the gown 116 such that the protective guard 100 may seal the interface 101 between the glove cuff 114 and the gown cuff 118. The protective guard 100 may be worn over both the glove cuff 114 and the gown cuff 118, or in other embodiments, the protective guard 100 may extend under the glove cuff 114 or the gown cuff 118. Further, although shown and described herein as separate from the glove 112 and the gown 116, it will be appreciated that the protective guard 100 could be formed as part of the glove 112 and/or the gown 116. Moreover, although shown and described herein with respect to one protective guard 100, one glove 112 and one sleeve and cuff 118 of a gown 116, it will be understood that a protective guard 100 may be used to seal the interface 101 between each glove and sleeve of the gown worn by the user. Additionally or alternatively, the protective guard 100 may be used to seal other interfaces 101 of a surgeon's protective clothing or equipment or to seal interfaces 101 between other wearable items worn by other users in other settings.

In the exemplary embodiment depicted in FIG. 2, the gown cuff 118 extends under the glove cuff 114. For instance, a user of the protective guard 100, such as a surgeon, may first don the gown 116, positioning the gown cuff 118 at or near the user's wrist. Next, the user may don the glove 112, positioning the glove cuff 114 over the gown cuff 118 and forming an interface 101 between the glove 112 and the gown 116.

After donning the gown 116 and the glove 112, the user may don the protective guard 100 such that the proximal segment 104 may be positioned at or near the user's hand H. In the exemplary embodiment of FIG. 2, the proximal segment 104 of the protective guard 100 is positioned at or near a portion of the user's hand H near the user's wrist W. As depicted in FIG. 2, the proximal segment 104 may define a thumbhole 120 for receipt of the user's thumb T. For instance, the user's thumb T may be inserted through the thumbhole 120, e.g., to assist the user in donning the protective guard 100 and/or to help keep the protective guard 100 in position. Thus, using the thumbhole 120 may help the user attain the best fit and placement for the protective guard 100.

As further illustrated in FIG. 2, the distal segment 106 may be positioned over the user's arm A. In some embodiments, the distal segment 106 may be positioned at the user's forearm, or in other embodiments, the distal segment 106 may be positioned above the user's elbow. As described above, each of the proximal segment 104 and the distal segment 106 may comprise a superabsorbent adhesive such that each of the proximal segment 104 and the distal segment 106 may adhere or attach to the material that the segment 104, 106 overlies. For instance, an adhesive may be applied to or incorporated into an inner surface 104a of the proximal segment 104 such that the proximal segment 104 may adhere to the glove 112. Similarly, an adhesive may be applied to or incorporated into an inner surface 106a of the distal segment 106 such that the distal segment 106 may adhere to the gown 116. By adhering to the underlying material, the proximal segment 104 and distal segment 106 may help prevent fluid from flowing beneath the protective guard 100 and, thereby, may help prevent fluid from reaching the interface 101 between the glove 112 and gown 116. Further, as previously described, the superabsorbent material from which the proximal segment 104 and the distal segment 106 may be formed may absorb fluid that contacts the proximal segment 104 and/or the distal segment 106. By absorbing fluid, the proximal segment 104 and/or the distal segment 106 may help reduce or eliminate fluid flowing over the protective guard 100 and, thereby, may help reduce or eliminate fluid available to flow under the protective guard 100 and to the interface 101.

Referring back to FIG. 1, the proximal segment 104 has a length $l_p$, and the distal segment 106 has a length $l_d$. In some embodiments, the length $l_p$ of the proximal segment 104 may be equal to the length Id of the distal segment 106. In other embodiments, one of the proximal segment 104 and the distal segment 106 may have an extended length. For example, the length $l_p$ of the proximal segment 104 may be longer than the length $l_d$ of the distal segment 106, or the length $l_d$ of the distal segment 106 may be longer than the length $l_p$ of the proximal segment 104. The extended length of one of the segments 104, 106 may help the user don the protective guard 100. For instance, the extra length of the longer segment 104, 106 may provide the user a tab or the like to hold or grasp as the user is wrapping the protective guard 100 about his or her arm A and hand H. Additionally or alternatively, the extra length of the longer segment 104, 106 may allow the user to customize the fit of the protective guard 100 and/or may ensure that the protective guard 100 is securely fastened to the user.

Moreover, the proximal segment 104 may have a width $w_p$ and the distal segment 106 may have a width $w_d$. The width $w_p$ of the proximal segment 104 and/or the width $w_d$ of the distal segment 106 may vary between embodiments of the protective guard 100. For instance, the widths $w_p$, $w_d$ may vary from relatively narrow to relatively broad, which may allow various embodiments of the proximal and distal segments 104, 106 of the protective guard 100 to have different levels of fluid absorption and flow control (e.g., to accommodate different quantities and rates of fluid flow), as well as different degrees of fit with respect to, e.g., a glove 112 and/or a gown 116 (FIGS. 2, 3) as discussed herein. As an example, a protective guard 100 having a proximal segment 104 with a narrower width $w_p$ may be used in situations in which the proximal segment 104 is exposed to less fluid (e.g., in an operation involving less fluid or when the flow of fluid may be concentrated toward the distal segment 106, which may have a wider width $w_d$ in such situations) such that the proximal segment 104 is required to absorb and control less fluid than in other situations. As another example, a wider proximal segment 104, i.e., a strap 100 with a broader width $w_p$, may be used, e.g., in situations in which a flow of fluid is concentrated toward the proximal segment 104 or a tighter or more secure fit is desired between the protective guard 100 and an underlying material, such as a gown and/or glove, at the proximal segment 104. That is, a wider proximal segment 104 may provide a greater or more contact area between the protective guard 100 and the underlying material at the proximal segment 104 to allow a better, tighter, and/or more secure fit between the strap 100 and the underlying material. It will be appreciated that the width $w_d$ of the distal segment 106 may vary from narrow to wide for similar reasons as described with respect to the proximal segment 104 and/or for other, different reasons. In some embodiments, the widths $w_p$, $w_d$ may range from about one half of one inch (½ in.) to about six inches (6 in.); more particularly, the widths $w_p$, $w_d$ may range from about one inch (1 in.) to about four inches (4 in.).

As depicted in FIG. 2 and as discussed with respect to FIG. 1, the protective guard 100 may include a body segment 108 of superabsorbent material. The body segment 108 extends lengthwise along the body 102 from the proximal segment 104 to the distal segment 106. As shown in FIG. 2, the body segment 108 may run or extend along the user's arm A. In some embodiments, the body segment 108 may be positioned with respect to the user's arm A to be in an area in which fluid is more likely to collect. For example, in embodiments in which the protective guard 100 extends above the user's elbow, the body segment 108 may be positioned such that the body segment 108 extends over the inside of the user's elbow, i.e., in the crease of the user's arm A at the elbow. The body segment 108 may be positioned in other locations as well. Further, it will be appreciated that, in some embodiments, the protective guard 100 may include multiple body segments 108 extending along the body 102 of the protective guard 100. Each body segment 108 may extend from the proximal segment 104 to the distal segment 106, or one or more of the body segments 108 may not span the entire distance between the proximal segment 104 and distal segment 106. In some embodiments, one or more body segments 108 may protective guard a relatively small area of the body 102 and, for instance, may be circular, square, triangular, or any other suitable shape. Additionally or alternatively, the body segment 108 may have any suitable width $w_b$, and the width $w_b$ of the body segment 108 may vary between embodiments of the protective guard 100, e.g., the width $w_b$ of the body segment 108 may vary from relatively narrow to relatively broad, which may allow various embodiments of the body segment 108 of the protective guard 100 to have different levels of fluid absorption and flow control (e.g., to accommodate different quantities and rates of fluid flow). Moreover, one or more of the body segments 108 may be formed from various different superabsorbent materials having different levels of fluid absorption and flow control. For instance, an outermost body segment 108 may be formed from a superabsorbent material enabling fast fluid absorption configured to channel fluid via capillarity of the superabsorbent fibers to an inner body segment 108 that is configured to absorb a higher volume of fluid to function as a reservoir for fluid absorption.

Referring now to FIG. 3, in some embodiments, the proximal segment 104 may be positioned below the user's thumb T, e.g., over the heel of the user's hand H or closer to the user's wrist W. More particularly, the user may don the gown 116 and glove 112 as described above with respect to FIG. 2. Then, rather than positioning the thumb T through a thumbhole 120 in the proximal segment 104, the proximal segment may be wrapped about the user's hand H and/or wrist W below the user's thumb T. In other embodiments, the glove cuff 114 may be positioned under or inward from the gown cuff 118, i.e., the gown cuff 118 may be drawn down over the glove cuff 114 rather than the glove cuff 114 being pulled over top of the gown cuff 118. Then, the protective guard 100 may be donned to cover the interface 101 between the glove cuff 114 and the gown cuff 118. In still other embodiments, the user may wear a second glove 112 on top of a first glove 112, and a cuff 114 of the second glove 112 may extend over at least a portion of the protective guard 100. For instance, the first glove cuff 114 and the gown cuff 118 may be positioned under the protective guard 100 as described herein, and the user may don the second glove 112 after the protective guard 100 is secured in place such that the second glove cuff 114 extends over at least a portion of the protective guard 100.

In yet other embodiments, such as illustrated in FIG. 3, the protective guard 100 may be worn over the sleeve of the gown 116 but under the glove cuff 114. More particularly, the user may don the gown 116, then don the protective guard 100 such that the protective guard 100 extends beyond the gown cuff 118 toward the user's hand H, and finally don the glove 112, pulling the glove cuff 114 over at least a portion of the protective guard 100. In such embodiments, the protective guard 100 protects or seals the interface 101 between the gown cuff 118 and glove cuff 114 by extending between the gown 116 and glove 112, with the proximal segment 104 positioned on the first side 103 of the interface 101 and the distal segment 106 positioned on the second side 105 of the interface 101 as previously described. Further, rather than the adhesive of the proximal segment 104 being applied on an inner surface 104a of the proximal segment 104, the adhesive may be applied on an outer surface 104b of the proximal segment 104. As such, the proximal segment 104 may adhere to the glove 112 as described herein and not to the user.

In still other embodiments, the proximal segment 104 and/or the distal segment 106 may be formed from other materials than a superabsorbent material as described above. For example, the proximal segment 104 may be formed from an elastic material that is not superabsorbent, such that the proximal segment 104 may be an elastic band of material, and the distal segment 106 may be a band of a material such as nitrile. The elastic material may be a material that includes elastic filaments (e.g., LYCRA® fiber, a type of spandex fiber). In other embodiments, one of the proximal segment 104 and the distal segment 106 may be formed from an elastic, non-superabsorbent material while the other of the proximal and distal segments 104, 106 is formed from a superabsorbent material as described herein. In further embodiments, the proximal segment 104 and/or the distal segment 106 may be formed from an expandable material that begins in a non-expanded state and, upon interacting with fluid, absorbs the fluid and creates a pressure seal once expanded. More particularly, the expandable material may be a cotton, non-woven, or type of fabric other than a superabsorbent that absorbs fluid and increases in volume. Thus, in some embodiments, the proximal segment 104 and/or the distal segment 106 may be formed from a material other than a superabsorbent material. It will be appreciated that, in any of the described embodiments, the body 102 may be formed from a fluid impervious material, such as a fluid impervious film or the like. The body segment 108 may be formed from a superabsorbent or non-superabsorbent material as described herein. For instance, the body segment 108 may be formed from an expandable, non-superabsorbent material that expands upon contacting or interacting with fluid.

Turning now to FIGS. 4A through 5B, one or more surfaces of the protective guard 100 may comprise patterning or the like, e.g., to help guide fluid that contacts the protective guard away from the interface 101 and/or to help the protective guard 100 remain in position with respect to the interface 101. For example, the protective guard 100 may include ribs, nubs, or other surface topography on the inside of the protective guard 100 to prevent slippage and/or on the outside of the protective guard 100 to channel fluid away from the interface 101 or into a fluid reservoir such as the superabsorbent material. Referring to FIGS. 4A-4C, in some embodiments, the body 102 of the protective guard 100 may comprise an outer surface 110 having a first raised pattern. The first raised pattern may be material, such as the fluid impervious material from which the body 102 is formed, that projects away from the outer surface 110 to define the first raised pattern. The first raised pattern may be configured to help channel or guide fluid away from the interface 101. In some embodiments, the first raised pattern may be configured to guide fluid toward the superabsorbent material, for example, toward the proximal segment 104, the distal segment 106, and/or the body segment 108, such that, e.g., the superabsorbent or non-superabsorbent expandable material may absorb and retain the fluid.

As shown in FIG. 4A, the first raised pattern may comprise vertical striations. In other embodiments, as illustrated in FIG. 4B, the first raised pattern may comprise a honeycomb pattern. In yet other embodiments, as depicted in FIG. 4C, the first raised pattern may comprise cross-hatching. It will be understood that the vertical striations, honeycomb, and cross-hatching shown in FIGS. 4A-4C are provided by way of example only, and other raised patterns also may be used, in addition to or in lieu of the illustrated first raised patterns. Further, the first raised pattern need not be uniform over the body 102, e.g., a combination of patterns may be used to form the first raised pattern, the elements of the first raised pattern may be larger or smaller in various locations of the outer surface 110, and/or the elements of the first raised pattern may have variable spacing over the outer surface 110 (e.g., some elements may be closer together at one location of the outer surface 110 than at a second location of the outer surface 110). Moreover, the entire outer surface 110 need not comprise the first raised pattern; that is, in some embodiments, the first raised pattern may extend over the entire outer surface 110, but in other embodiments, the first raised pattern may extend over only one or more portions of the outer surface 110 but not the entire outer surface 110.

Figure 5A:
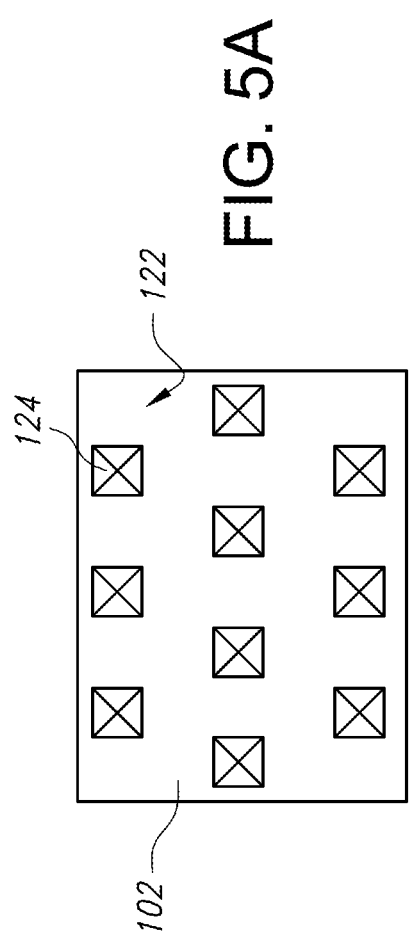
FIGS. 5A and 5B provide schematic views of a second raised pattern for an inner surface of the protective guard of FIG. 1, according to various exemplary embodiments of the present subject matter.
Figure 5B:
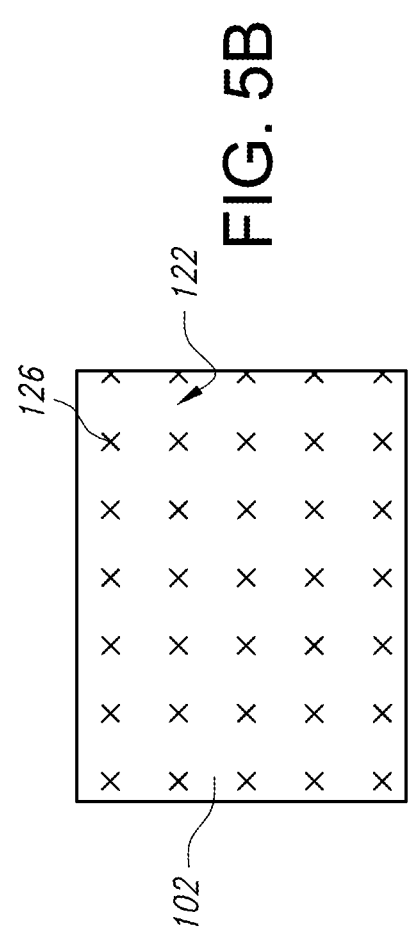

Referring to FIGS. 5A and 5B, in some embodiments, the body 102 of the protective guard 100 may comprise an inner surface 122 having a second raised pattern. In some embodiments, the body 102 may comprise both the first raised pattern on the outer surface 110 and the second raised pattern on the inner surface 122. However, in other embodiments, the body 102 may comprise only one raised pattern, either the first raised pattern on the outer surface 110 or the second raised pattern on the inner surface 122.

The second raised pattern on the inner surface 122 of the protective guard body 102 may help provide a better grip between the protective guard 100 and the material the protective guard 100 surrounds or overlies, which may help provide a better fit between the protective guard 100 and the material it surrounds or overlies. For instance, as illustrated in FIG. 5A, the second raised pattern may comprise pyramidal shaped nubs 124. In other embodiments, such as depicted in FIG. 5B, the second raised pattern may comprise X shaped nubs 126. It will be appreciated that the pyramidal shaped nubs 124 and X shaped nubs 126 shown in FIGS. 5A and 5B are provided by way of example only, and other raised patterns also may be used, in addition to or in lieu of the illustrated second raised patterns. Further, the second raised pattern need not be uniform over the body 102, e.g., a combination of patterns may be used to form the second raised pattern, the elements of the second raised pattern may be larger or smaller in various locations of the inner surface 122, and/or the elements of the second raised pattern may have variable spacing over the inner surface 122 (e.g., some elements may be closer together at one location of the inner surface 122 than at a second location of the inner surface 122). Moreover, the entire inner surface 122 need not comprise the second raised pattern; that is, in some embodiments, the second raised pattern may extend over the entire inner surface 122, but in other embodiments, the second raised pattern may extend over only one or more portions of the inner surface 122 but not the inner surface 122.

In some embodiments, bands, patterns, or the like may be included on the proximal segment 104 and/or the distal segment 106, e.g., to create a torturous path for the fluid that further hinders fluid flow into the interface 101. For instance, the proximal segment 104 may include the first raised pattern on an outer surface of the proximal segment 104 and/or the second raised pattern on an inner surface of the proximal segment 104. In further embodiments, the distal segment 106 may include the first raised pattern on an outer surface of the distal segment 106 and/or the second raised pattern on an inner surface of the distal segment 106. It will be appreciated that one or both of the proximal and distal segments 104, 106 may include such banding, patterning, or the like on one or both of their inner and outer surfaces to help discourage the flow of fluid to the interface 101. As one example, a proximal segment 104 formed from a non-superabsorbent expandable material may include the first raised pattern on its outer surface and the second raised pattern on its inner surface to create a tortuous path for the fluid as it flows on, over, or against the proximal segment 104, which may lengthen the time the fluid is in contact with the proximal segment 104 and thereby allow more time for the expandable material to absorb the fluid.

It will be understood that, although described herein as an accessory or a standalone unit, the protective guard 100 could be integrated into a wearable item. More particularly, the protective guard 100 described herein with respect to the glove 112 and gown 116 may be described as a protective gauntlet, providing a barrier between the user's skin and a patient's bodily fluids. In some embodiments, the protective guard 100 may be integrated into the glove 112, or in other embodiments, the protective guard 100 may be integrated into the sleeve of the gown 116.

Figure 6:
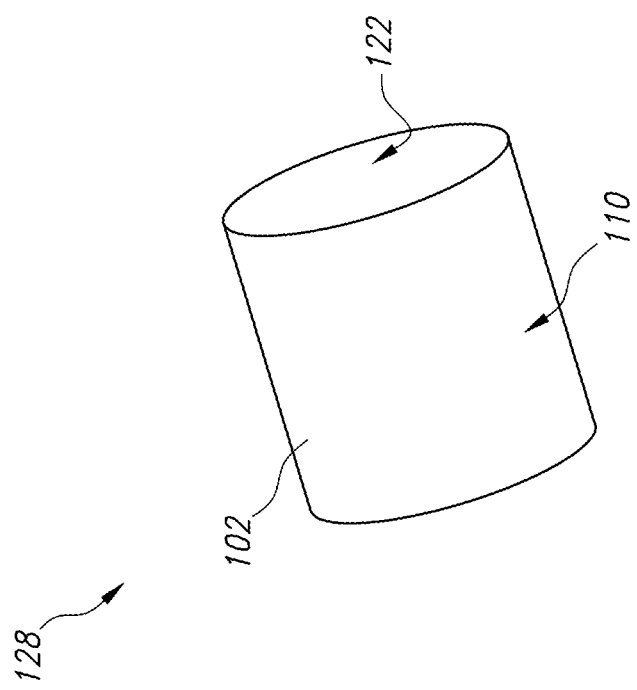
FIG. 6 provides a schematic view of a cuff for sealing an interface, according to an exemplary embodiment of the present subject matter.

Additionally or alternatively, components of the protective guard 100 may be used separately from the protective guard 100, e.g., as standalone features, to seal an interface 101. For example, referring to FIG. 6, the body 102 could be formed as a cuff 128 that a user pulls over an interface 101 between two interfacing items, e.g., the glove 112 and gown 116 described herein. More particularly, rather than a flat piece of material having the proximal segment 104 along its proximal edge and the distal segment 106 along its distal edge, the body 102 may be formed as a generally cylindrical or frustoconical piece of material such that the body 102 is similar to a cuff. When formed from an elastic fluid impervious material as described herein (e.g., nitrile or the like), the cuff 128 formed from the body 102 may be positioned over the interface 101 and may compress the material beneath the cuff 128. Moreover, the cuff 128 may be configured as described herein with respect to the body 102, e.g., the cuff 128 may include a first raised pattern on its outer surface 110 and/or a second raised pattern on its inner surface 122. Accordingly, the cuff 128 formed from the body 102 may help prevent fluid from flowing or seeping beneath the cuff 128, thereby helping keep fluid away from the interface 101. Further, compressing the material beneath the cuff 128 may help prevent the material beneath the cuff 128, e.g., the gown 116, from bunching up or otherwise forming channels that may direct fluid toward the interface 101.

As another example, the proximal segment 104 and/or the distal segment 106 could be used separately from the body 102. For instance, the adhesive segment(s) 104, 106 may be used like tape. More specifically, referring to FIGS. 7A and 7B, the segment(s) 104, 106 may be formed as a tape 130 that may be wrapped at, above, and/or below the interface 101 to tape the interface 101 closed. The adhesive may be applied on an inner surface and/or an outer surface of the tape 130, such that the tape 130 may be positioned over or under one or more interfacing items, such as the glove 112 and gown 116 described herein. Like the proximal and distal segments 104, 106, the tape 130 may include a superabsorbent material, and the superabsorbent material in the tape 130 may absorb fluid that contacts the tape 130, helping to reduce the amount of fluid that could breach the interface 101. In other embodiments, in addition to or in lieu of comprising an adhesive, the tape 130 may be formed from a material that sticks to itself, e.g., such that the tape 130 may be wrapped back on itself to form a pressure seal. In still other embodiments, in addition to or in lieu of comprising an adhesive, the tape 130 may comprise hooks formed, e.g., in a substrate supporting the superabsorbent material, that catch on material such as the material from which the gown 116 is made to secure the tape 130 in place. In yet other embodiments, in addition to or in lieu of comprising an adhesive, other types of fasteners, such as hook and loop fasteners, ties, snaps, etc. may be used to secure the tape 130 to itself and/or to another component, such as the gown 116 or glove 112.

Accordingly, the present subject matter provides several benefits and advantages. For instance, the present subject matter provides a protective guard that creates a seal between interfacing items, such as at the interface between surgical gown sleeves and gloves. The seal helps, e.g., prevent channeling of blood and other fluids underneath the glove and contaminating a user's bare hands. The protective guard may be used by the user as an accessory to current personal protective equipment or may be incorporated into a gown sleeve or glove. The protective guard may include a fluid impervious elastic material with a textured surface that provides fluid pathway patterning and/or a textured surface that allows the protective guard to stay in position. The protective guard may be configured as a gauntlet design and may include an adhesive or the like to form a seal between an interface, such as a gown-glove interface, to help prevent channeling and potential contamination. The protective guard also may include an absorbent material, e.g., to collect any fluid that seeps past the initial seal. Further, the absorbent material may be configured to swell when exposed to a fluid such as blood, thereby creating a better pressure seal. Additionally or alternatively, the adhesive may react with the water in blood to quickly polymerize and create a seal. The protective guard may include a thumbhole to ease donning and to help keep the protective guard in place.

Further, the protective guard may include a tab to help with donning the protective guard, e.g., the tab may provide a place to hold the protective guard when donning it. When used with a glove and gown, the protective guard may extend from a glove cuff to above the user's elbow, providing protection and preventing the gown sleeve from sliding downward. In some embodiments, components of the protective guard, such as an elastic fluid impervious material forming the body of the protective guard or a superabsorbent material forming an edge segment of the protective guard, may be used separately from the protective guard. For example, a cuff formed from the elastic fluid impervious material may be used to extend the competency of a glove and prevent channeling between a glove and gown sleeve interface. As another example, a tape may be formed from the superabsorbent material and may be wrapped around two interfacing items to form a seal at the interface between the items. Other benefits and advantages also may be realized from the present subject matter.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A protective guard for sealing an interface, the protective guard comprising:
    a body comprising a fluid impervious material, wherein the fluid impervious material of the body comprises an outer surface having a first raised pattern, the body further comprising a body segment comprising an absorbent material;
    a proximal segment; and
    a distal segment,
    wherein at least one of the proximal segment and the distal segment comprises a first superabsorbent material, and wherein the absorbent material of the body segment comprises a second superabsorbent material,
    wherein the proximal segment is configured to be positioned on a first side of the interface and the distal segment is configured to be positioned on a second side of the interface,
    wherein the protective guard is configured to extend about the interface to create a fluid barrier, and
    wherein at least one of the proximal segment and the distal segment comprises an adhesive configured to form a seal, wherein the adhesive is a superabsorbent adhesive configured to polymerize when the superabsorbent adhesive comes into contact with water, and
    wherein first superabsorbent material is configured to absorb fluid at a different fluid absorption rate than the second superabsorbent material.

2. The protective guard of claim 1, wherein the fluid impervious material is hydrophobic.

3. The protective guard of claim 1, wherein the fluid impervious material has elasticity.

4. The protective guard of claim 1, wherein the fluid impervious material is nitrile.

5. The protective guard of claim 1, wherein at least one of the proximal segment and the distal segment comprises an outer surface having a second raised pattern.

6. The protective guard of claim 5, wherein the raised pattern comprises vertical striations.

7. The protective guard of claim 5, wherein the raised pattern comprises a honeycomb pattern.

8. The protective guard of claim 5, wherein the raised pattern comprises cross-hatching.

9. The protective guard of claim 1, wherein at least one of the proximal segment and the distal segment comprises an inner surface having an inner surface raised pattern.

10. The protective guard of claim 9, wherein the raised pattern of the inner surface comprises pyramidal shaped nubs.

11. The protective guard of claim 9, wherein the raised pattern of the inner surface comprises X shaped nubs.

12. The protective guard of claim 1, wherein the proximal segment is configured to be positioned at a user's hand.

13. The protective guard of claim 1, wherein the proximal segment comprises an elastic material.

14. The protective guard of claim 1, wherein the distal segment comprises nitrile.

15. The protective guard of claim 1, wherein at least one of the proximal segment and the distal segment further comprises a non-superabsorbent material that expands upon contact with a fluid.

16. A protective guard for sealing an interface, the protective guard comprising:
    a body comprising a fluid impervious material, the body further comprising a body segment, wherein the fluid impervious material of the body comprises an outer surface having a raised pattern;
    a proximal segment comprising an elastic material; and
    a distal segment comprising nitrile,
    wherein the proximal segment is configured to be positioned on a first side of the interface and the distal segment is configured to be positioned on a second side of the interface,
    wherein the protective guard is configured to extend about the interface to create a fluid barrier,
    wherein at least one of the proximal segment and the distal segment comprises an adhesive configured to form a seal, wherein the adhesive is a superabsorbent adhesive configured to polymerize when the superabsorbent adhesive comes into contact with water,
    wherein at least one of the proximal segment and the distal segment comprises a first superabsorbent material, and wherein the body segment comprises a second superabsorbent material, and
    wherein first superabsorbent material is configured to absorb fluid at a different fluid absorption rate than the second superabsorbent material.

17. The protective guard of claim 16, wherein the fluid impervious material is a fluid impervious film.

18. The protective guard of claim 16, wherein at least one of an inner surface and an outer surface of the proximal segment has a proximal segment raised pattern.

19. The protective guard of claim 16, wherein at least one of an inner surface and an outer surface of the distal segment has a distal segment raised pattern.

* * * * *